(12) United States Patent
Qian

(10) Patent No.: US 9,707,202 B2
(45) Date of Patent: *Jul. 18, 2017

(54) CERTAIN CHEMICAL ENTITIES, COMPOSITIONS, AND METHODS

(71) Applicant: NEUPHARMA, INC., Foster City, CA (US)

(72) Inventor: Xiangping Qian, Foster City, CA (US)

(73) Assignee: NeuPharma, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/044,424

(22) Filed: Feb. 16, 2016

(65) Prior Publication Data

US 2016/0303066 A1 Oct. 20, 2016

Related U.S. Application Data

(63) Continuation of application No. 14/342,348, filed as application No. PCT/US2012/052910 on Aug. 29, 2012, now Pat. No. 9,328,081.

(60) Provisional application No. 61/530,360, filed on Sep. 1, 2011.

(51) Int. Cl.

| A61K 31/325 | (2006.01) |
| C07D 295/205 | (2006.01) |
| C07C 271/44 | (2006.01) |
| C07D 211/60 | (2006.01) |
| C07D 295/192 | (2006.01) |
| A61K 31/4453 | (2006.01) |
| A61K 31/495 | (2006.01) |
| A61K 31/535 | (2006.01) |

(52) U.S. Cl.
CPC ........ *A61K 31/325* (2013.01); *A61K 31/4453* (2013.01); *A61K 31/495* (2013.01); *A61K 31/535* (2013.01); *C07C 271/44* (2013.01); *C07D 211/60* (2013.01); *C07D 295/192* (2013.01); *C07D 295/205* (2013.01)

(58) Field of Classification Search
CPC .............. A61K 31/325; A61K 31/4425; A61K 31/495; A61K 31/535
See application file for complete search history.

(56) References Cited

U.S. PATENT DOCUMENTS

| 5,846,514 A | 12/1998 | Foster et al. |
| 6,334,997 B1 | 1/2002 | Foster et al. |
| 9,328,081 B2 | 5/2016 | Qian |
| 2005/0209195 A1 | 9/2005 | Menta et al. |
| 2009/0326275 A1 | 12/2009 | Dimauro |
| 2010/0010232 A1 | 1/2010 | Neupert et al. |
| 2010/0048901 A1 | 2/2010 | Takahashi et al. |
| 2015/0072984 A1 | 3/2015 | Qian |

FOREIGN PATENT DOCUMENTS

| WO | WO-9722596 A1 | 6/1997 |
| WO | WO-9730035 A1 | 8/1997 |
| WO | WO-9732856 A1 | 9/1997 |
| WO | WO-9813354 A1 | 4/1998 |
| WO | WO-9902166 A1 | 1/1999 |
| WO | WO-0040529 A1 | 7/2000 |
| WO | WO-0041669 A2 | 7/2000 |
| WO | WO-0047212 A1 | 8/2000 |
| WO | WO-0192224 A1 | 12/2001 |
| WO | WO-0204434 A1 | 1/2002 |
| WO | WO-0208213 A1 | 1/2002 |
| WO | WO-2008051474 A1 | 5/2008 |
| WO | WO-2010074971 A1 | 7/2010 |
| WO | WO-2011094671 A2 | 8/2011 |
| WO | WO-2012154564 A1 | 11/2012 |

OTHER PUBLICATIONS

European search report and opinion dated Apr. 16, 2015 for EP Application No. 12827951.
Higuchi, et al. Pro-drugs as novel drug delivery systems. American Chemical Society. ACS symposium series 14. 1975.
International search report and written opinion dated Nov. 2, 2012 for PCT/US2012/052910.
Notice of allowance dated Dec. 15, 2015 for U.S. Appl. No. 14/342,348.
Office action dated Jul. 8, 2015 for U.S. Appl. No. 14/342,348.

*Primary Examiner* — Craig Ricci
*Assistant Examiner* — Christopher R Stone
(74) *Attorney, Agent, or Firm* — Wilson, Sonsini, Goodrich & Rosati

(57) ABSTRACT

Chemical entities that are curcumin derivatives, pharmaceutical compositions and methods of treatment of cancer are described.

18 Claims, No Drawings

CERTAIN CHEMICAL ENTITIES, COMPOSITIONS, AND METHODS

This application claims the benefit of U.S. Patent Application No. 61/530,360, filed on Sep. 1, 2011, which is hereby incorporated by reference.

Provided are certain chemical entities that are curcumin derivatives, pharmaceutical compositions and methods thereof that may be useful in the treatment of cancer.

Cancer can be viewed as a breakdown in the communication between tumor cells and their environment, including their normal neighboring cells. Signals, both growth-stimulatory and growth-inhibitory, are routinely exchanged between cells within a tissue. Normally, cells do not divide in the absence of stimulatory signals, and likewise, will cease dividing in the presence of inhibitory signals. In a cancerous, or neoplastic state, a cell acquires the ability to "override" these signals and to proliferate under conditions in which normal cells would not grow.

Curcumin is the principal curcuminoid of the popular Indian spice turmeric, which is a member of the ginger family (Zingiberaceae). It has been shown to exhibit anticancer activity in several cancer cell lines and animal models. Its clinical applications, however, have been limited due to its poor solubility and low bioavailability.

Provided is at least one chemical entity chosen from compounds of Formula I

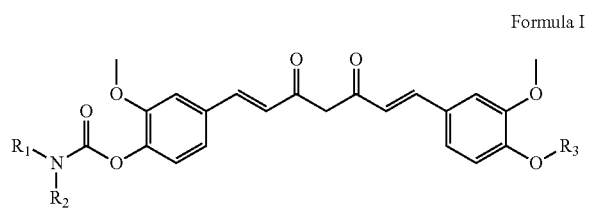

Formula I and pharmaceutically acceptable salts thereof, wherein $R_1$ is chosen from hydrogen, optionally substituted alkyl, optionally substituted cycloalkyl, optionally substituted heterocycloalkyl, optionally substituted aryl, and optionally substituted heteroaryl;

$R_2$ is chosen from optionally substituted alkyl, optionally substituted cycloalkyl, optionally substituted heterocycloalkyl, optionally substituted aryl, and optionally substituted heteroaryl;

or $R_1$ and $R_2$ may optionally be joined together with any intervening atoms to form an optionally substituted heterocycloalkyl ring; and $R_3$ is chosen from hydrogen, optionally substituted alkyl, optionally substituted cycloalkyl, optionally substituted heterocycloalkyl, optionally substituted aryl, optionally substituted heteroaryl, optionally substituted acyl, optionally substituted aminocarbonyl, optionally substituted aminosulfonyl, optionally substituted alkoxycarbonyl, and optionally substituted phosphato.

Also provided is a pharmaceutical composition comprising a pharmaceutically acceptable carrier and at least one chemical entity described herein.

Also provided is a packaged pharmaceutical composition comprising a pharmaceutical composition described herein and instructions for using the composition to treat a subject suffering from cancer.

Also provided is a method of treating cancer in a subject which comprises administering to a subject in need thereof a therapeutically effective amount of at least one chemical entity described herein.

As used herein, the following words and phrases are generally intended to have the meanings as set forth below, except to the extent that the context in which they are used indicates otherwise.

The following abbreviations and terms have the indicated meanings throughout:

AcOH=acetic acid
Boc=tert-butoxycarbonyl
c-=cyclo
DCC=dicyclohexylcarbodiimide
DIEA=N,N-diisopropylethylamine
DMAP=4-dimethylaminopyridine
EDC=1-ethyl-3-(3-dimethylaminopropyl) carbodiimide
eq=equivalent(s)
Et=ethyl
EtOAc or EA=ethyl acetate
EtOH=ethanol
g=gram
h or hr=hour
HBTU=O-(benzotriazol-1-yl)-N,N,N',N'-tetramethyluronium hexafluorophosphate
HOBt=hydroxybenzotriazole
HPLC=high pressure liquid chromatography
i-=iso
kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
mg=milligram
min=minute
mL=milliliter
mmol=millimole
n-=normal
NaOAc=sodium acetate
PE=petroleum ether
Ph=phenyl
Prep=preparative
quant.=quantitative
RP-HPLC=reverse phase-high pressure liquid chromatography
rt or RT=room temperature
s-=sec-=secondary
t-=tert-=tertiary
THF=tetrahydrofuran
TLC=thin layer chromatography
UV=ultraviolet As used herein, when any variable occurs more than one time in a chemical formula, its definition on each occurrence is independent of its definition at every other occurrence.

As used herein, a dash ("-") that is not between two letters or symbols is used to indicate a point of attachment for a substituent. For example, —CONH$_2$ is attached through the carbon atom.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, "alkyl" refers to straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

As used herein, "alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

As used herein, "alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons.

As used herein, "cycloalkyl" refers to a non-aromatic carbocyclic ring, usually having from 3 to 8 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to six carbons.

As used herein, "mono- and di-alkylcarboxamide" refers to a group of the formula —(C=O)NR$_a$R$_b$ wherein R$_a$ and R$_b$ are independently chosen from hydrogen and alkyl groups of the indicated number of carbon atoms, provided that R$_a$ and R$_b$ are not both hydrogen.

As used herein, "acyl" refers to the groups H—C(O)—; (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C=O)$—.

As used herein, "formyl" refers to the group —C(O)H.

As used herein, "carboxy" and/or "carboxyl" refer to the group —C(O)OH.

As used herein, "alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

As used herein, "acyloxy" refers to (acyl)-O—.

As used herein, "alkoxycarbonyloxy" refers to (alkoxycarbonyl)-O—.

As used herein, "azido" refers to the group —$N_3$.

As used herein, "amino" refers to the group —$NH_2$.

As used herein, "mono- and di-(alkyl)amino" refers to secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, "aminocarbonyl" and "aminosulfonyl" refer to the groups —CONR$^b$R$^c$ and —SO$_2$NR$^b$R$^c$ respectively, where R$^b$ is chosen from H, optionally substituted $C_1$-$C_6$ alkyl, optionally substituted cycloalkyl, optionally substituted heterocycloalkyl, optionally substituted aryl, and optionally substituted heteroaryl, optionally substituted alkoxy; and R$^c$ is chosen from hydrogen and optionally substituted $C_1$-$C_4$ alkyl; or R$^b$ and R$^c$ taken together with the nitrogen to which they are bound, form an optionally substituted 4- to 8-membered nitrogen-containing heterocycloalkyl which optionally includes 1 or 2 additional heteroatoms chosen from O, N, and S in the heterocycloalkyl ring;

where each substituted group is independently substituted with one or more substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —SO₂NH(C₁-C₄ alkyl), —SO₂NH(phenyl), —NHSO₂(C₁-C₄ alkyl), —NHSO₂(phenyl), and —NHSO₂(C₁-C₄ haloalkyl).

As used herein, "aryl" refers to: 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 4- to 8-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

As used herein, "aryloxy" refers to the group —O-aryl.

As used herein, "aralkyl" refers to the group -alkyl-aryl.

As used herein, "carbamimidoyl" refers to the group —C(=NH)—NH2.

As used herein, "substituted carbamimidoyl" refers to the group —C(=NR$^e$)—NR$^f$R$^g$ where R$^e$ is chosen from hydrogen, cyano, optionally substituted alkyl, optionally substituted cycloalkyl, optionally substituted aryl, optionally substituted heteroaryl, and optionally substituted heterocycloalkyl; and R$^f$ and R$^g$ are independently chosen from hydrogen optionally substituted alkyl, optionally substituted cycloalkyl, optionally substituted aryl, optionally substituted heteroaryl, and optionally substituted heterocycloalkyl, provided that at least one of R$^e$, R$^f$, and R$^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from —R$^a$, —OR$^b$, optionally substituted amino (including —NR$^c$COR$^b$, —NR$^c$CO₂R$^a$, —NR$^c$CONR$^b$R$^c$, —NR$^b$C(NR$^c$)NR$^b$R$^c$, —NR$^b$C(NCN)NR$^b$R$^c$, and —NR$^b$SO₂R$^a$), halo, cyano, nitro, oxo (as a substituent for cycloalkyl, heterocycloalkyl, and heteroaryl), optionally substituted acyl (such as —COR$^b$), optionally substituted alkoxycarbonyl (such as —CO₂R$^b$), aminocarbonyl (such as —CONR$^b$R$^c$), —OCOR$^b$, —OCO₂R$^a$, —OCONR$^b$R$^c$, —OP(O)(OR$^b$)OR$^c$, sulfanyl (such as SR$^b$), sulfinyl (such as —SOR$^a$), and sulfonyl (such as —SO₂R$^a$ and —SO₂NR$^b$R$^c$), where R$^a$ is chosen from optionally substituted C₁-C₆ alkyl, optionally substituted aryl, and optionally substituted heteroaryl;

R$^b$ is chosen from H, optionally substituted C₁-C₆ alkyl, optionally substituted aryl, and optionally substituted heteroaryl; and R$^c$ is chosen from hydrogen and optionally substituted C₁-C₄ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently chosen from C₁-C₄ alkyl, aryl, heteroaryl, aryl-C₁-C₄ alkyl-, heteroaryl-C₁-C₄ alkyl-, C₁-C₄ haloalkyl, —OC₁-C₄ alkyl, —OC₁-C₄ alkylphenyl, —C₁-C₄ alkyl-OH, —OC₁-C₄ haloalkyl, halo, —OH, —NH₂, —C₁-C₄ alkyl-NH₂, —N(C₁-C₄ alkyl)(C₁-C₄ alkyl), —NH(C₁-C₄ alkyl), —N(C₁-C₄ alkyl)(C₁-C₄ alkylphenyl), —NH(C₁-C₄ alkylphenyl), cyano, nitro, oxo (as a substituent for cycloalkyl, heterocycloalkyl, or heteroaryl), —CO₂H, —C(O)OC₁-C₄ alkyl, —CON(C₁-C₄ alkyl)(C₁-C₄ alkyl), —CONH(C₁-C₄ alkyl), —CONH₂, —NHC(O)(C₁-C₄ alkyl), —NHC(O)(phenyl), —N(C₁-C₄ alkyl)C(O)(C₁-C₄ alkyl), —N(C₁-C₄ alkyl)C(O)(phenyl), —C(O)C₁-C₄ alkyl, —C(O)C₁-C₄ phenyl, —C(O)C₁-C₄ haloalkyl, —OC(O)C₁-C₄ alkyl, —SO2(C₁-C₄ alkyl), —SO₂(phenyl), —SO₂(C₁-C₄ haloalkyl), —SO₂NH₂, —SO₂NH(C₁-C₄ alkyl), —SO₂NH(phenyl), —NHSO₂(C₁-C₄ alkyl), —NHSO₂(phenyl), and —NHSO₂(C₁-C₄ haloalkyl).

As used herein, "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

As used herein, "heteroaryl" refers to:

5- to 7-membered aromatic, monocyclic rings containing one or more, for example, from 1 to 4, or in certain embodiments, from 1 to 3, heteroatoms chosen from N, O, and S, with the remaining ring atoms being carbon;

bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridazinyl, triazolyl, quinolinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—O$^-$) substituents, such as pyridinyl N-oxides.

As used herein, "heterocycloalkyl" refers to a single, non-aromatic ring, usually with 3 to 8 ring atoms, containing at least 2 carbon atoms in addition to 1-3 heteroatoms independently chosen from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, and 2,5-piperizinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—O$^-$) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 8 ring atoms, contains at least 2 carbon atoms in addition to 1-3 heteroatoms independently chosen from oxygen, sulfur, and nitrogen, as well as combinations comprising at least one of the foregoing heteroatoms; and the other ring, usually with 3 to 8 ring atoms, optionally contains 1-3 heteroatoms independently chosen from oxygen, sulfur, and nitrogen and is not aromatic.

As used herein, "sulfanyl" refers to the groups: —S-(optionally substituted ($C_1$-$C_6$)alkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

As used herein, "sulfinyl" refers to the groups: —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

As used herein, "sulfonyl" refers to the groups: —S(O$_2$)-(optionally substituted ($C_1$-$C_6$)alkyl), —S(O$_2$)-optionally substituted aryl), —S(O$_2$)-optionally substituted heteroaryl), —S(O$_2$)-(optionally substituted heterocycloalkyl), and —S(O$_2$)-(optionally substituted amino).

As used herein, "substituted" refers to any one or more hydrogens on the designated atom or group is replaced with a selection from the indicated group, provided that the designated atom's normal valence is not exceeded. When a substituent is oxo (i.e. =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

As used herein, the terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, azido, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted cycloalkyl, optionally substituted heterocycloalkyl, optionally substituted alkenyl, optionally substituted alkynyl, optionally substituted aryl, and optionally substituted heteroaryl; $R^b$ is chosen from hydrogen, optionally substituted $C_1$-$C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkyl-phenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

As used herein, "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently chosen from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)$ $OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkyl-phenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

As used herein, "substituted alkoxy" refers to alkoxy wherein the alkyl constituent is substituted (i.e. —O-(substituted alkyl)) wherein "substituted alkyl" refers to alkyl wherein one or more (such as up to 5, for example, up to 3) hydrogen atoms are replaced by a substituent independently chosen from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)$ $OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkyl-phenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

In some embodiments, a substituted alkoxy group is "polyalkoxy" or —O— (optionally substituted alkylene)-(optionally substituted alkoxy), and includes groups such as —$OCH_2CH_2OCH_3$, and residues of glycol ethers such as polyethyleneglycol, and —$O(CH_2CH_2O)_xCH_3$, where x is an integer of 2-20, such as 2-10, and for example, 2-5. Another substituted alkoxy group is hydroxyalkoxy or —$OCH_2(CH_2)_yOH$, where y is an integer of 1-10, such as 1-4.

As used herein, "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^6SO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R_a$, —$OCONR^bR^c$, —$OP(O)(OR^b)$ $OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkyl-phenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

As used herein, "substituted amino" refers to the group —NHR$^d$ or —NR$^d$R$^e$ wherein R$^d$ is chosen from hydroxy, formyl, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and wherein R$^e$ is chosen from optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from —R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl or heterocycloalkyl), optionally substituted acyl (such as —COR$^b$), optionally substituted alkoxycarbonyl (such as —CO$_2$R$^b$), aminocarbonyl (such as —CONR$^b$R$^c$, —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is chosen from optionally substituted C$_1$-C$_6$ alkyl, optionally substituted alkenyl, optionally substituted alkynyl, optionally substituted aryl, and optionally substituted heteroaryl;

R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently chosen from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl or heterocycloalkyl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl); and wherein optionally substituted acyl, optionally substituted alkoxycarbonyl, sulfinyl and sulfonyl are as defined herein.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

The term "phosphato" refers to —OP(O)(OR$^b$)OR$^c$ where R$^b$ is selected from hydrogen, optionally substituted C$_1$-C$_6$ alkyl, optionally substituted cycloalkyl, optionally substituted heterocycloalkyl, optionally substituted aryl, and optionally substituted heteroaryl; and R$^c$ is independently selected from hydrogen and optionally substituted C$_1$-C$_4$ alkyl. In some embodiments, R$^b$ and R$^c$ are hydrogen.

Compounds of Formula I include, but are not limited to, optical isomers of compounds of Formula I, racemates, and other mixtures thereof. In those situations, the single enantiomers or diastereomers, i.e. optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with carbon-carbon double bonds. Where compounds of Formula I exists in various tautomeric forms, chemical entities described herein include all tautomeric forms of the compound.

Compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates (including hydrates), unsolvated polymorphs (including anhydrates), conformational polymorphs, and amorphous forms, as well as mixtures thereof, unless a particular crystalline or amorphous form is referred to. Similarly, "pharmaceutically acceptable salts of compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the pharmaceutically acceptable salts, as well as mixtures thereof.

A "solvate" is formed by the interaction of a solvent and a compound. The term "compound" is intended to include solvates of compounds. Similarly, "pharmaceutically acceptable salts" includes solvates of pharmaceutically acceptable salts. Suitable solvates are pharmaceutically acceptable solvates, such as hydrates, including monohydrates and hemi-hydrates.

Compounds of Formula I also include other pharmaceutically acceptable forms of the recited compounds, including chelates, non-covalent complexes, prodrugs, and mixtures thereof.

A "chelate" is formed by the coordination of a compound to a metal ion at two (or more) points. The term "compound" is intended to include chelates of compounds. Similarly, "pharmaceutically acceptable salts" includes chelates of pharmaceutically acceptable salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound'. Similarly, "pharmaceutically acceptable salts" includes "non-covalent complexes" of pharmaceutically acceptable salts.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry.

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen group containing a ring nitrogen or a heteroaryl group containing a ring nitrogen.

The compounds disclosed herein can be used in different enriched isotopic forms, e.g., enriched in the content of $^2H$, $^3H$, $^{11}C$, $^{13}C$ and/or $^{14}C$. In one particular embodiment, the compound is deuterated at least one position. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)]2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

"Prodrugs" described herein include any compound that becomes a compound of Formula I when administered to a subject, e.g., upon metabolic processing of the prodrug. Similarly, "pharmaceutically acceptable salts" includes "prodrugs" of pharmaceutically acceptable salts. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, $(C_1-C_{18})$-alkyl, $(C_3-C_7)$-cycloalkyl, $(C_3-C_7)$-cycloalkyl-$(C_1-C_4)$-alkyl-, $(C_6-C_{14})$-aryl which is unsubstituted or substituted by a residue $(C_1-C_2)$-alkyl, $(C_1-C_2)$-alkoxy, fluoro, or chloro; heteroaryl-, $(C_6-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

As used herein the terms "group", "radical" or "fragment" are synonymous and are intended to indicate functional groups or fragments of molecules attachable to a bond or other fragments of molecules.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

As used herein, "active agent" is used to indicate a chemical entity which has biological activity. In certain embodiments, an "active agent" is a compound having pharmaceutical utility. For example an active agent may be an anti-cancer therapeutic.

As used herein, "significant" refers to any detectable change that is statistically significant in a standard parametric test of statistical significance such as Student's T-test, where $p<0.05$.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, "therapeutically effective amount" of a chemical entity described herein refers to an amount effective, when administered to a human or non-human subject, to provide a therapeutic benefit such as amelioration of symptoms, slowing of disease progression, or prevention of disease.

"Treating" or "treatment" encompasses administration of at least one compound of Formula I, or a pharmaceutically acceptable salt thereof, to a subject, particularly a human, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

As used herein, "cancer" refers to all types of cancer or neoplasm or malignant tumors found in mammals, including carcinomas and sarcomas. Examples of cancer are cancer of the brain, breast, cervix, colon, head & neck, kidney, lung, non-small cell lung, melanoma, mesothelioma, ovary, sarcoma, stomach, uterus and Medulloblastoma.

As used herein, "subject" refers to a mammal that has been or will be the object of treatment, observation or experiment. The methods described herein can be useful in both human therapy and veterinary applications. In some embodiments, the subject is a human.

The term "mammal" is intended to have its standard meaning, and encompasses humans, dogs, cats, sheep, and cows, for example.

Also provided is at least one chemical entity chosen from compounds of Formula I

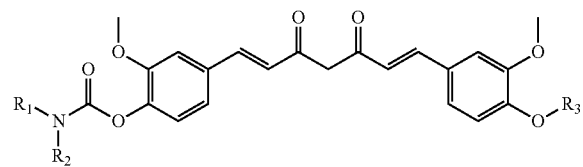

Formula I and pharmaceutically acceptable salts thereof, wherein $R_1$ is chosen from hydrogen, optionally substituted alkyl, optionally substituted cycloalkyl, optionally substituted heterocycloalkyl, optionally substituted aryl, and optionally substituted heteroaryl;

$R_2$ is chosen from optionally substituted alkyl, optionally substituted cycloalkyl, optionally substituted heterocycloalkyl, optionally substituted aryl, and optionally substituted heteroaryl;

or $R_1$ and $R_2$ may optionally be joined together with any intervening atoms to form an optionally substituted heterocycloalkyl ring; and $R_3$ is chosen from hydrogen, optionally substituted alkyl, optionally substituted cycloalkyl, optionally substituted heterocycloalkyl, optionally substituted aryl, optionally substituted heteroaryl, optionally substituted acyl, optionally substituted aminocarbonyl, optionally substituted aminosulfonyl, optionally substituted alkoxycarbonyl, and optionally substituted phosphato.

In some embodiments, $R_1$ is chosen from hydrogen, optionally substituted alkyl, optionally substituted cycloalkyl, and optionally substituted heterocycloalkyl. In some embodiments, $R_1$ is chosen from optionally substituted lower alkyl. In some embodiments, $R_1$ is lower alkyl optionally substituted with amino, mono-(alkyl)amino, di-(alkyl)amino, or heterocycloalkyl. In some embodiments, $R_1$ is lower alkyl optionally substituted with amino, mono-(alkyl)amino, di-(alkyl)amino, pyrrolidin-1-yl, or morpholin-1-yl.

In some embodiments, $R_2$ is chosen from optionally substituted alkyl, optionally substituted cycloalkyl, and optionally substituted heterocycloalkyl. In some embodiments, $R_2$ is optionally substituted alkyl. In some embodiments, $R_2$ is lower alkyl.

In some embodiments, $R_1$ and $R_2$ are independently chosen from optionally substituted alkyl.

In some embodiments, $R_1$ and $R_2$ are joined together to form an optionally substituted 4- to 8-membered heterocycloalkyl ring.

In some embodiments, $R_1$ and $R_2$ are joined together to form an optionally substituted pyrrolidin-1-yl, morpholin-1-yl, piperidin-1-yl, piperazin-1-yl, 1,4-diazepan-1-yl, and 1,4-diazocan-1-yl. In some embodiments, $R_1$ and $R_2$ are joined together to form a heterocycloalkyl ring chosen from pyrrolidin-1-yl, morpholin-1-yl, piperidin-1-yl, piperazin-1-yl, 1,4-diazepan-1-yl, and 1,4-diazocan-1-yl, each of which is optionally substituted with one or two groups independently chosen from hydroxyl, amino, oxo, and lower alkyl optionally substituted with hydroxy or amino.

In some embodiments, $R_3$ is chosen from hydrogen, optionally substituted alkyl, optionally substituted cycloalkyl, optionally substituted heterocycloalkyl, optionally substituted aryl, optionally substituted heteroaryl, optionally substituted aminocarbonyl, and optionally substituted phosphato.

In some embodiments, $R_3$ is chosen from hydrogen, optionally substituted alkyl, optionally substituted cycloalkyl, optionally substituted heterocycloalkyl, optionally substituted aminocarbonyl, and optionally substituted phosphato.

In some embodiments, $R_3$ is chosen from hydrogen, optionally substituted lower alkyl, and optionally substituted aminocarbonyl.

In some embodiments, $R_3$ is chosen from hydrogen and optionally substituted lower alkyl.

In some embodiments, $R_3$ is hydrogen.

In some embodiments, $R_3$ is optionally substituted lower alkyl. In some embodiments, $R_3$ is lower alkyl optionally substituted with hydroxyl or amino. In some embodiments, $R_3$ is chosen from methyl, 2-aminoethyl, and 2-hydroxyethyl. In some embodiments, $R_3$ is methyl.

In some embodiments, $R_3$ is optionally substituted aminocarbonyl. In some embodiments, $R_3$ is —$CONR^bR^c$ where
$R^b$ is chosen from hydrogen and $C_1$-$C_6$ alkyl; and
$R^c$ is chosen from hydrogen and $C_1$-$C_4$ alkyl; or
$R^b$ and $R^c$ taken together with the nitrogen to which they are bound, form a 4- to 8-membered nitrogen-containing heterocycloalkyl which optionally includes 1 or 2 additional heteroatoms chosen from O, N, and S in the heterocycloalkyl ring and which is optionally substituted with one or two groups independently chosen from hydroxyl, amino, oxo, and lower alkyl optionally substituted with hydroxyl.

In some embodiments, $R_3$ is —$CONR^bR^c$ where $R^b$ is chosen from hydrogen and $C_1$-$C_6$ alkyl; and $R^c$ is chosen from hydrogen and $C_1$-$C_4$ alkyl.

In some embodiments, $R_3$ is —$CONR^bR^c$ where $R^b$ and $R^c$ taken together with the nitrogen to which they are bound, form a ring chosen from pyrrolidin-1-yl, morpholin-1-yl, piperidin-1-yl, piperazin-1-yl, 1,4-diazepan-1-yl, and 1,4-diazocan-1-yl, each of which is optionally substituted with one or two groups independently chosen from hydroxyl, amino, oxo, and lower alkyl optionally substituted with hydroxyl. In some embodiments, $R_3$ is —$CONR^bR^c$ where $R^b$ and $R^c$ taken together with the nitrogen to which they are bound, form a piperazin-1-yl ring optionally substituted with one or two groups independently chosen from hydroxyl, amino, oxo, and lower alkyl optionally substituted with hydroxyl. In some embodiments, $R_3$ is —$CONR^bR^c$ where $R^b$ and $R^c$ taken together with the nitrogen to which they are bound, form a piperazin-1-yl ring.

Also provided is at least one chemical entity chosen from
4-((1E,6E)-7-(4-hydroxy-3-methoxyphenyl)-3,5-dioxohepta-1,6-dien-1-yl)-2-methoxyphenyl dimethylcarbamate,
4-((1E,6E)-7-(4-hydroxy-3-methoxyphenyl)-3,5-dioxohepta-1,6-dien-1-yl)-2-methoxyphenyl piperidine-1-carboxylate,
4-((1E,6E)-7-(4-hydroxy-3-methoxyphenyl)-3,5-dioxohepta-1,6-dien-1-yl)-2-methoxyphenyl 4-hydroxypiperidine-1-carboxylate,
4-((1E,6E)-7-(4-hydroxy-3-methoxyphenyl)-3,5-dioxohepta-1,6-dien-1-yl)-2-methoxyphenyl 4-aminopiperidine-1-carboxylate,
4-((1E,6E)-7-(4-hydroxy-3-methoxyphenyl)-3,5-dioxohepta-1,6-dien-1-yl)-2-methoxyphenyl 3-hydroxypiperidine-1-carboxylate,
4-((1E,6E)-7-(4-hydroxy-3-methoxyphenyl)-3,5-dioxohepta-1,6-dien-1-yl)-2-methoxyphenyl 3-aminopiperidine-1-carboxylate,
4-((1E,6E)-7-(4-hydroxy-3-methoxyphenyl)-3,5-dioxohepta-1,6-dien-1-yl)-2-methoxyphenyl piperazine-1-carboxylate,
4-((1E,6E)-7-(4-hydroxy-3-methoxyphenyl)-3,5-dioxohepta-1,6-dien-1-yl)-2-methoxyphenyl 4-methylpiperazine-1-carboxylate,
4-((1E,6E)-7-(4-hydroxy-3-methoxyphenyl)-3,5-dioxohepta-1,6-dien-1-yl)-2-methoxyphenyl 3-(hydroxymethyl)piperazine-1-carboxylate,
4-((1E,6E)-7-(4-hydroxy-3-methoxyphenyl)-3,5-dioxohepta-1,6-dien-1-yl)-2-methoxyphenyl 3-(hydroxymethyl)-4-methylpiperazine-1-carboxylate,
4-((1E,6E)-7-(4-hydroxy-3-methoxyphenyl)-3,5-dioxohepta-1,6-dien-1-yl)-2-methoxyphenyl morpholine-4-carboxylate,
4-((1E,6E)-7-(4-hydroxy-3-methoxyphenyl)-3,5-dioxohepta-1,6-dien-1-yl)-2-methoxyphenyl 2-(hydroxymethyl)morpholine-4-carboxylate,
4-((1E,6E)-7-(4-hydroxy-3-methoxyphenyl)-3,5-dioxohepta-1,6-dien-1-yl)-2-methoxyphenyl 2-(aminomethyl)morpholine-4-carboxylate,
4-((1E,6E)-7-(4-hydroxy-3-methoxyphenyl)-3,5-dioxohepta-1,6-dien-1-yl)-2-methoxyphenyl pyrrolidine-1-carboxylate,
4-((1E,6E)-7-(4-hydroxy-3-methoxyphenyl)-3,5-dioxohepta-1,6-dien-1-yl)-2-methoxyphenyl 3-hydroxypyrrolidine-1-carboxylate,
4-((1E,6E)-7-(4-hydroxy-3-methoxyphenyl)-3,5-dioxohepta-1,6-dien-1-yl)-2-methoxyphenyl 3-aminopyrrolidine-1-carboxylate,
4-((1E,6E)-7-(4-hydroxy-3-methoxyphenyl)-3,5-dioxohepta-1,6-dien-1-yl)-2-methoxyphenyl 3-(hydroxymethyl)pyrrolidine-1-carboxylate,
4-((1E,6E)-7-(4-hydroxy-3-methoxyphenyl)-3,5-dioxohepta-1,6-dien-1-yl)-2-methoxyphenyl 3-(aminomethyl)pyrrolidine-1-carboxylate,
4-((1E,6E)-7-(4-hydroxy-3-methoxyphenyl)-3,5-dioxohepta-1,6-dien-1-yl)-2-methoxyphenyl 1,4-diazepane-1-carboxylate,
4-((1E,6E)-7-(4-hydroxy-3-methoxyphenyl)-3,5-dioxohepta-1,6-dien-1-yl)-2-methoxyphenyl 4-methyl-1,4-diazepane-1-carboxylate,
4-((1E,6E)-7-(4-hydroxy-3-methoxyphenyl)-3,5-dioxohepta-1,6-dien-1-yl)-2-methoxyphenyl (2-aminoethyl)(methyl)carbamate,
4-((1E,6E)-7-(4-hydroxy-3-methoxyphenyl)-3,5-dioxohepta-1,6-dien-1-yl)-2-methoxyphenyl (2-(dimethylamino)ethyl)(methyl)carbamate,
4-((1E,6E)-7-(4-hydroxy-3-methoxyphenyl)-3,5-dioxohepta-1,6-dien-1-yl)-2-methoxyphenyl dimethylcarbamate,
4-((1E,6E)-7-(3,4-dimethoxyphenyl)-3,5-dioxohepta-1,6-dien-1-yl)-2-methoxyphenyl 3-aminopiperidine-1-carboxylate,
4-((1E,6E)-7-(4-(2-hydroxyethoxy)-3-methoxyphenyl)-3,5-dioxohepta-1,6-dien-1-yl)-2-methoxyphenyl 3-aminopiperidine-1-carboxylate,
4-((1E,6E)-7-(4-(2-hydroxyethoxy)-3-methoxyphenyl)-3,5-dioxohepta-1,6-dien-1-yl)-2-methoxyphenyl 4-aminopiperidine-1-carboxylate,
4-((1E,6E)-7-(3,4-dimethoxyphenyl)-3,5-dioxohepta-1,6-dien-1-yl)-2-methoxyphenyl piperazine-1-carboxylate,
4-((1E,6E)-7-(4-(2-hydroxyethoxy)-3-methoxyphenyl)-3,5-dioxohepta-1,6-dien-1-yl)-2-methoxyphenyl piperazine-1-carboxylate,
4-((1E,6E)-7-(4-((dimethylcarbamoyl)oxy)-3-methoxyphenyl)-3,5-dioxohepta-1,6-dien-1-yl)-2-methoxyphenyl piperazine-1-carboxylate,
((1E,6E)-3,5-dioxohepta-1,6-diene-1,7-diyl)bis(2-methoxy-4,1-phenylene)bis(piperazine-1-carboxylate),
4-((1E,6E)-7-(3,4-dimethoxyphenyl)-3,5-dioxohepta-1,6-dien-1-yl)-2-methoxyphenyl 4-methylpiperazine-1-carboxylate,
4-((1E,6E)-7-(3,4-dimethoxyphenyl)-3,5-dioxohepta-1,6-dien-1-yl)-2-methoxyphenyl 3-aminopyrrolidine-1-carboxylate,
4-((1E,6E)-7-(4-(2-hydroxyethoxy)-3-methoxyphenyl)-3,5-dioxohepta-1,6-dien-1-yl)-2-methoxyphenyl 3-aminopyrrolidine-1-carboxylate,
4-((1E,6E)-7-(3,4-dimethoxyphenyl)-3,5-dioxohepta-1,6-dien-1-yl)-2-methoxyphenyl 1,4-diazepane-1-carboxylate,
4-((1E,6E)-7-(4-hydroxy-3-methoxyphenyl)-3,5-dioxohepta-1,6-dien-1-yl)-2-methoxyphenyl methyl(2-(pyrrolidin-1-yl)ethyl)carbamate,
4-((1E,6E)-7-(4-hydroxy-3-methoxyphenyl)-3,5-dioxohepta-1,6-dien-1-yl)-2-methoxyphenyl methyl(2-morpholinoethyl)carbamate,
4-((1E,6E)-7-(3,4-dimethoxyphenyl)-3,5-dioxohepta-1,6-dien-1-yl)-2-methoxyphenyl piperidine-1-carboxylate,
4-((1E,6E)-7-(3,4-dimethoxyphenyl)-3,5-dioxohepta-1,6-dien-1-yl)-2-methoxyphenyl morpholine-4-carboxylate,
4-((1E,6E)-7-(4-(2-hydroxyethoxy)-3-methoxyphenyl)-3,5-dioxohepta-1,6-dien-1-yl)-2-methoxyphenyl piperidine-1-carboxylate,
4-((1E,6E)-7-(4-(2-hydroxyethoxy)-3-methoxyphenyl)-3,5-dioxohepta-1,6-dien-1-yl)-2-methoxyphenyl morpholine-4-carboxylate,
4-((1E,6E)-7-(4-(2-hydroxyethoxy)-3-methoxyphenyl)-3,5-dioxohepta-1,6-dien-1-yl)-2-methoxyphenyl dimethylcarbamate,
4-((1E,6E)-7-(4-(2-hydroxyethoxy)-3-methoxyphenyl)-3,5-dioxohepta-1,6-dien-1-yl)-2-methoxyphenyl 4-methylpiperazine-1-carboxylate,
4-((1E,6E)-7-(4-(2-hydroxyethoxy)-3-methoxyphenyl)-3,5-dioxohepta-1,6-dien-1-yl)-2-methoxyphenyl pyrrolidine-1-carboxylate,
4-((1E,6E)-7-(4-(2-hydroxyethoxy)-3-methoxyphenyl)-3,5-dioxohepta-1,6-dien-1-yl)-2-methoxyphenyl (2-aminoethyl)(methyl)carbamate, 4-((1E,6E)-7-(4-(2-hydroxyethoxy)-3-methoxyphenyl)-3,5-dioxohepta-1,6-dien-1-yl)-2-methoxyphenyl (2-(dimethylamino)ethyl)(methyl)carbamate,
4-((1E,6E)-7-(4-(2-hydroxyethoxy)-3-methoxyphenyl)-3,5-dioxohepta-1,6-dien-1-yl)-2-methoxyphenyl methyl(2-(pyrrolidin-1-yl)ethyl)carbamate,
4-((1E,6E)-7-(4-(2-hydroxyethoxy)-3-methoxyphenyl)-3,5-dioxohepta-1,6-dien-1-yl)-2-methoxyphenyl methyl(2-morpholinoethyl)carbamate,
4-((1E,6E)-7-(4-(2-aminoethoxy)-3-methoxyphenyl)-3,5-dioxohepta-1,6-dien-1-yl)-2-methoxyphenyl pyrrolidine-1-carboxylate,
4-((1E,6E)-7-(4-(2-aminoethoxy)-3-methoxyphenyl)-3,5-dioxohepta-1,6-dien-1-yl)-2-methoxyphenyl piperidine-1-carboxylate,
4-((1E,6E)-7-(4-(2-aminoethoxy)-3-methoxyphenyl)-3,5-dioxohepta-1,6-dien-1-yl)-2-methoxyphenyl morpholine-4-carboxylate,
4-((1E,6E)-7-(4-(2-aminoethoxy)-3-methoxyphenyl)-3,5-dioxohepta-1,6-dien-1-yl)-2-methoxyphenyl dimethylcarbamate,
4-((1E,6E)-7-(4-(2-aminoethoxy)-3-methoxyphenyl)-3,5-dioxohepta-1,6-dien-1-yl)-2-methoxyphenyl 4-methylpiperazine-1-carboxylate,
((1E,6E)-3,5-dioxohepta-1,6-diene-1,7-diyl)bis(2-methoxy-4,1-phenylene)bis(4-methylpiperazine-1-carboxylate),
2-methoxy-4-((1E,6E)-7-(3-methoxy-4-((piperidine-1-carbonyl)oxy)phenyl)-3,5-dioxohepta-1,6-dien-1-yl)phenyl piperazine-1-carboxylate,
4-((1E,6E)-7-(4-((dimethylcarbamoyl)oxy)-3-methoxyphenyl)-3,5-dioxohepta-1,6-dien-1-yl)-2-methoxyphenyl piperazine-1-carboxylate,
2-methoxy-4-((1E,6E)-7-(3-methoxy-4-((piperazine-1-carbonyl)oxy)phenyl)-3,5-dioxohepta-1,6-dien-1-yl)phenyl morpholine-4-carboxylate,
2-methoxy-4-((1E,6E)-7-(3-methoxy-4-((pyrrolidine-1-carbonyl)oxy)phenyl)-3,5-dioxohepta-1,6-dien-1-yl)phenyl piperazine-1-carboxylate, and
2-methoxy-4-((1E,6E)-7-(3-methoxy-4-((4-methylpiperazine-1-carbonyl)oxy)phenyl)-3,5-dioxohepta-1,6-dien-1-yl)phenyl morpholine-4-carboxylate,
and pharmaceutically acceptable salts thereof.

The chemical entities described herein may exhibit increased solubility as compared with curcumin. The solubility of the chemical entities described herein can be tested as described below. Certain of the chemical entities described herein displayed a solubility of at least twice that of curcumin when tested under such conditions. Certain of the chemical entities described herein displayed a solubility of at least ten times that of curcumin when tested under such conditions. Certain of the chemical entities described herein displayed a solubility of at least hundred times that of curcumin when tested under such conditions.

The chemical entities described herein can be synthesized utilizing techniques well known in the art from commercially available starting materials and reagents. The desired product can be purified from the reaction mixture by standard methods, e.g. by extraction and/or silica gel chromatography or high-pressure liquid chromatography.

The chemical entities described herein may be used in treating a variety of cancers. Cancers that can be prevented and/or treated by the chemical entities, compositions, and methods described herein include, but are not limited to, human sarcomas and carcinomas, e.g. carcinomas, e.g., colon carcinoma, pancreatic cancer, breast cancer, ovarian cancer, prostate cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the chemical entities described herein are used for the treatment of cancers of the (i) digestive system including, without limitation, the esophagus, stomach, small intestine, colon (including colorectal), liver & intrahepatic bile duct, gallbladder & other biliary, pancreas, and other digestive organs;

(ii) respiratory system, including without limitation, larynx, lung & bronchus, and other respiratory organs;

(iii) breast;

(iv) genital system, including without limitation, uterine cervix, ovary, and prostate;

(v) urinary system, including without limitation, urinary bladder and kidney and renal pelvis; and (vi) oral cavity & pharynx, including without limitation, tongue, mouth, pharynx, and other oral cavity.

In some embodiments, the chemical entities described herein are used for the treatment of colorectal cancer, liver cancer, lung cancer, breast cancer and oral cancer.

Chemical entities described herein having the desired pharmacological activity may be administered, in some embodiments, as a pharmaceutically acceptable composition comprising an pharmaceutical excipient, to a subject, as described herein. Depending upon the manner of introduction, the chemical entities may be formulated in a variety of ways as discussed below. The concentration of the at least one chemical entity in the formulation may vary from about 0.01-100 wt. %.

The administration of the chemical entities described herein can be done in a variety of ways, including, but not limited to, orally, subcutaneously, intravenously, intranasally, transdermally, intraperitoneally, intramuscularly, intrapulmonary, vaginally, rectally, or intraocularly.

Pharmaceutical dosage forms include at least one chemical entity described herein and one or more pharmaceutical excipients. As is known in the art, pharmaceutical excipients are secondary ingredients which function to enable or enhance the delivery of a drug or medicine in a variety of dosage forms (e.g.: oral forms such as tablets, capsules, and liquids; topical forms such as dermal, ophthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 21$^{st}$ Edition, Lippincott Williams & Wilkins (2005); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995), each of which is incorporated herein by reference for all purposes.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colors, flavors, sweetening agents, polymers, waxes or other solubility-retarding materials.

Compositions for intravenous administration will generally comprise intravenous fluids, i.e., sterile solutions of simple chemicals such as sugars, amino acids or electrolytes, which can be easily carried by the circulatory system and assimilated.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington: The Science and Practice of Pharmacy, Lippincott Williams & Wilkins (2005). The pH of such IV fluids may vary, and will typically be from 3.5 to 8 as known in the art.

The chemical entities described herein may also be used in conjunction with other well known therapeutic agents that are selected for their particular usefulness against the condition that is being treated. For example, the chemical entities described herein may be useful in combination with at least one additional anti-cancer and/or cytotoxic agents. Further, the chemical entities described herein may also be useful in combination with other inhibitors of parts of the signaling pathway that links cell surface growth factor receptors to nuclear signals initiating cellular proliferation.

Such known anti-cancer and/or cytotoxic agents that may be used in combination with the chemical entities described herein include:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycinC, dactinomycin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase such as finasteride;

(iii) anti-invasion agents [for example c-Src kinase family inhibitors like 4-(6-chloro-2,3methylenedioxyanilino)-7-[2-(4-methylpiperazin-1-yl)ethoxy]-5-tetrahydropyran-4yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4ylamino}thiazole-5-carboxamide (dasatinib, BMS-354825; J. Med. Chem., 2004, 47, 66586661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB 1 antibody cetuximab [Erbitux, C225] and any growth factor or growth factor receptor antibodies disclosed by Stem et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifamib (RI15777) and lonafamib (SCH66336)), inhibitors of cell signalling through MEK and/or AKT kinases, c-kit inhibitors, abl kinase inhibitors, P13 kinase inhibitors, Plt3 kinase inhibitors, CSF-IR kinase inhibitors, IGF receptor (insulin like growth factor) kinase inhibitors; aurora kinase inhibitors (for example AZD1152, PH739358, VX-680, MLN8054, R763, MP235, MP529, VX-528 and AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4.{4-fluoro-2-methylindol-5-yloxy)-6-methoxy-7-(3pyrrolidin-1-ylpropoxy) quinazoline (AZD2171; Example 240 within WO 00/47212), compounds such as those disclosed in International Patent Applications WO 97/22596, WO 97/30035, WO 97/32856 and WO 98/13354 and compounds that work by other mechanisms (for example linomide, inhibitors of integrin av~3 function and angiostatin));

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase subject tolerance to chemotherapy or radiotherapy such as multi-drug resistance gene therapy; and (x) immunotherapy approaches, including for example ex-vivo and in-vivo approaches to increase the immunogenicity of subject's tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies.

In certain embodiments, the at least one chemical entity is administered in combination with one or more agents chosen from pacliataxel, bortezomib, dacarbazine, gemcitabine, trastuzumab, bevacizumab, capecitabine, docetaxel, erlotinib, aromatase inhibitors, such as AROMASIN™ (exemestane), and estrogen receptor inhibitors, such as FASLODEX™ (fulvestrant).

When a chemical entity described herein is administered into a human subject, the daily dosage will normally be determined by the prescribing physician with the dosage generally varying according to the age, weight, and response of the individual subject, as well as the severity of the subject's symptoms.

In one exemplary application, a suitable amount of at least one chemical entity is administered to a subject undergoing treatment for cancer, for example, breast cancer. Administration typically occurs in an amount of between about 0.01 mg/kg of body weight to about 100 mg/kg of body weight per day (administered in single or divided doses), such as at least about 0.1 mg/kg of body weight per day. A particular therapeutic dosage can include, e.g., from about 0.01 mg to about 1000 mg of the chemical entity, such as including, e.g., from about 1 mg to about 1000 mg. The quantity of the at least one chemical entity in a unit dose of preparation may be varied or adjusted from about 0.1 mg to 1000 mg, such as from about 1 mg to 300 mg, for example 10 mg to 200 mg, according to the particular application. The amount administered will vary depending on the particular $IC_{50}$ value of the at least one chemical entity used and the judgment of the attending clinician taking into consideration factors such as health, weight, and age. In combinational applications in which the at least one chemical entity described herein is not the sole active ingredient, it may be possible to administer lesser amounts of the at least one chemical entity and still have therapeutic or prophylactic effect.

In some embodiments, the pharmaceutical preparation is in unit dosage form. In such form, the preparation is subdivided into unit doses containing appropriate quantities of the active component, e.g., an effective amount to achieve the desired purpose.

The actual dosage employed may be varied depending upon the requirements of the subject and the severity of the condition being treated. Determination of the proper dosage for a particular situation is within the skill of the art. Generally, treatment is initiated with smaller dosages which are less than the optimum dose of the at least one chemical entity. Thereafter, the dosage is increased by small amounts until the optimum effect under the circumstances is reached. For convenience, the total daily dosage may be divided and administered in portions during the day if desired.

The amount and frequency of administration of the at least one chemical entities described herein, and if applicable other chemotherapeutic agents and/or radiation therapy, will be regulated according to the judgment of the attending clinician (physician) considering such factors as age, condition and size of the subject as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the subject, and in view of the observed responses of the disease to the administered therapeutic agents.

Also, in general, the at least one chemical entities described herein need not be administered in the same pharmaceutical composition as a chemotherapeutic agent, and may, because of different physical and chemical characteristics, be administered by a different route. For example, the chemical entities/compositions may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemical entity (and where appropriate, chemotherapeutic agent and/or radiation) will depend upon the diagnosis of the attending physicians and their judgment of the condition of the subject and the appropriate treatment protocol.

The chemical entities described herein (and where appropriate chemotherapeutic agent and/or radiation) may be administered concurrently (e.g., simultaneously, essentially simultaneously or within the same treatment protocol) or sequentially, depending upon the nature of the proliferative disease, the condition of the subject, and the actual choice of chemotherapeutic agent and/or radiation to be administered in conjunction (i.e., within a single treatment protocol) with the chemical entity/composition.

In combinational applications and uses, the chemical entity/composition and the chemotherapeutic agent and/or radiation need not be administered simultaneously or essentially simultaneously, and the initial order of administration of the chemical entity/composition, and the chemotherapeutic agent and/or radiation, may not be important. Thus, the at least one chemical entity described herein may be administered first followed by the administration of the chemotherapeutic agent and/or radiation; or the chemotherapeutic agent and/or radiation may be administered first followed by the administration of the at least one chemical entity described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the subject. For example, the chemotherapeutic agent and/or radiation may be administered first, and then the treatment continued with the administration of the at least one chemical entity described herein followed, where determined advantageous, by the administration of the chemotherapeutic agent and/or radiation, and so on until the treatment protocol is complete.

Thus, in accordance with experience and knowledge, the practicing physician can modify each protocol for the administration of a chemical entity/composition for treatment according to the individual subject's needs, as the treatment proceeds.

The attending clinician, in judging whether treatment is effective at the dosage administered, will consider the general well-being of the subject as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

EXAMPLES

The following examples serve to more fully describe the manner of using the invention. These examples are presented for illustrative purposes and should not serve to limit the true scope of the invention.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

Example 1: Preparation of 4-((1E,6E)-7-(3,4-dimethoxyphenyl)-3,5-dioxohepta-1,6-dien-1-yl)-2-methoxyphenyl morpholine-4-carboxylate

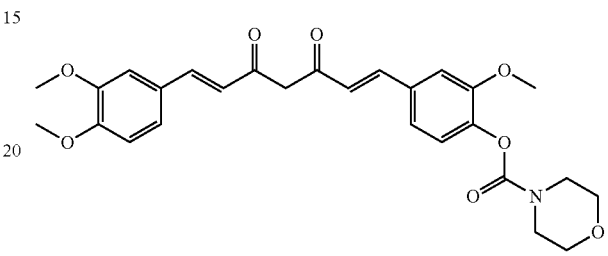

4-((1E,6E)-7-(3,4-dimethoxyphenyl)-3,5-dioxohepta-1,6-dien-1-yl)-2-methoxyphenyl morpholine-4-carboxylate

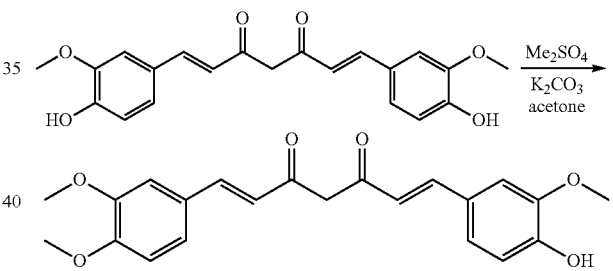

To the solution of (1E,6E)-1,7-bis(4-hydroxy-3-methoxyphenyl)hepta-1,6-diene-3,5-dione (368 mg, 1.0 mmol, 1.0 eq.) in dry acetone (10 mL) were added anhydrous $K_2CO_3$ (138 mg, 1.0 mmol, 1.0 eq.) and sulfuric acid dimethyl ester (176 mg, 1.0 mmol, 1.0 eq.) at rt. The reaction mixture was heated under reflux overnight, cooled, diluted with water and extracted with $CH_2Cl_2$ (30 mL×3). The combined organic layers were washed with $H_2O$, dried over anhydrous $Na_2SO_4$ and concentrated. The resulting residue was purified by silica column chromatography using $CH_2Cl_2$ as eluent to provide (1E,6E)-1-(3,4-dimethoxyphenyl)-7-(4-hydroxy-3-methoxyphenyl)hepta-1,6-diene-3,5-dione (170 mg, 44%).

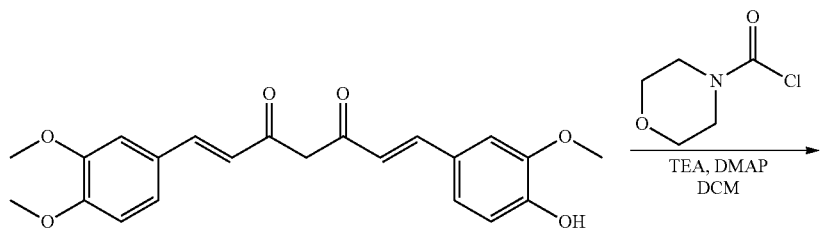

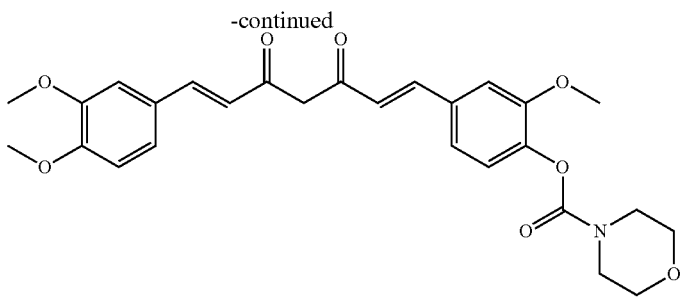

To a solution of (1E,6E)-1-(3,4-dimethoxyphenyl)-7-(4-hydroxy-3-methoxyphenyl)hepta-1,6-diene-3,5-dione (100 mg, 0.26 mmol, 1.0 eq.), TEA (53 mg, 0.52 mmol, 2.0 eq.) and DMAP (3 mg, 0.026 mmol, 0.1 eq.) in DCM (5 mL) was added morpholine-4-carbonyl chloride (39 mg, 0.26 mmol, 1.0 eq.) at rt. The resulting mixture stirred at rt overnight, then concentrated. The resulting residue was dissolved in EA (10 mL), washed with aqueous NaHCO3 solution, dried over Na$_2$SO$_4$ and concentrated. The resulting residue was purified using RP-HPLC to afford 4-((1E,6E)-7-(3,4-dimethoxyphenyl)-3,5-dioxohepta-1,6-dien-1-yl)-2-methoxyphenyl morpholine-4-carboxylate (29.5 mg, 23%) as an orange solid. LRMS (M+H$^+$) m/z calculated 496.2. found 496.1. $^1$H NMR (CDCl$_3$, 400 MHz) δ 7.59-7.65 (dd, 2H), 7.08-7.17 (m, 5H), 6.89 (d, 1H), 6.49-6.57 (dd, 2H), 5.84 (s, 1H), 3.94 (s, 3H), 3.92 (s, 3H), 3.89 (s, 3H), 3.74-3.77 (m, 4H), 3.58-3.71 (m, 4H).

Example 2: Preparation of 4-((1E,6E)-7-(3,4-dimethoxyphenyl)-3,5-dioxohepta-1,6-dien-1-yl)-2-methoxyphenyl 4-methylpiperazine-1-carboxylate

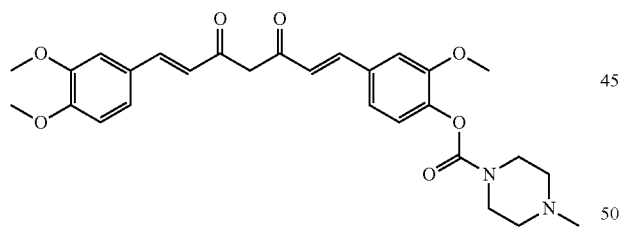

4-((1E,6E)-7-(3,4-dimethoxyphenyl)-3,5-dioxohepta-1,6-dien-1-yl)-2-methoxyphenyl 4-methylpiperazine-1-carboxylate 4-((1E,6E)-7-(3,4-dimethoxyphenyl)-3,5-dioxohepta-1,6-dien-1-yl)-2-methoxyphenyl 4-methylpiperazine-1-carboxylate was prepared as described for 4-((1E,6E)-7-(3,4-dimethoxyphenyl)-3,5-dioxohepta-1,6-dien-1-yl)-2-methoxyphenyl morpholine-4-carboxylate (67 mg, 51%). LRMS (M+H$^+$) m/z calculated 509.2. found 509.2. $^1$H NMR (CDCl$_3$, 400 MHz) δ 7.54-7.61 (dd, 2H), 7.04-7.13 (m, 5H), 6.84 (d, 1H), 6.46-6.54 (dd, 2H), 5.81 (s, 1H), 3.91 (s, 3H), 3.89 (s, 3H), 3.85 (s, 3H), 3.60-3.72 (m, 4H), 2.41-2.55 (m, 4H), 2.36 (s, 3H).

Example 3: Preparation of 4-((1E,6E)-7-(3,4-dimethoxyphenyl)-3,5-dioxohepta-1,6-dien-1-yl)-2-methoxyphenyl dimethylcarbamate

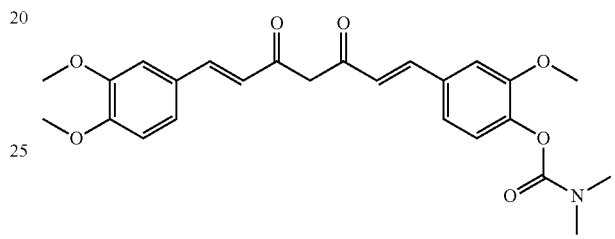

4-((1E,6E)-7-(3,4-dimethoxyphenyl)-3,5-dioxohepta-1,6-dien-1-yl)-2-methoxyphenyl dimethylcarbamate 4-((1E,6E)-7-(3,4-dimethoxyphenyl)-3,5-dioxohepta-1,6-dien-1-yl)-2-methoxyphenyl dimethylcarbamate was prepared as described for 4-((1E,6E)-7-(3,4-dimethoxyphenyl)-3,5-dioxohepta-1,6-dien-1-yl)-2-methoxyphenyl morpholine-4-carboxylate (43 mg, 36%) as an orange solid. LRMS (M+H+) m/z calculated 454.2. found 454.2. $^1$H NMR (CDCl$_3$, 400 MHz) δ 7.58-7.64 (dd, 2H), 7.08-7.16 (m, 5H), 6.88 (d, 1H), 6.48-6.56 (dd, 2H), 5.84 (s, 1H), 3.93 (s, 3H), 3.92 (s, 3H), 3.87 (s, 3H), 3.13 (s, 3H), 3.02 (s, 3H).

Example 4: Preparation of 4-((1E,6E)-7-(3,4-dimethoxyphenyl)-3,5-dioxohepta-1,6-dien-1-yl)-2-methoxyphenyl piperidine-1-carboxylate

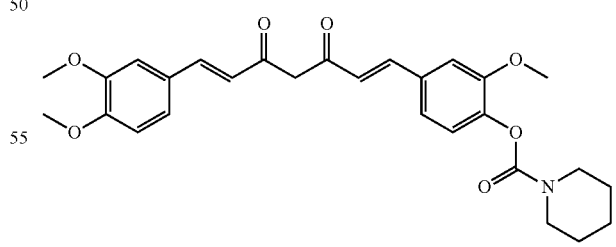

4-((1E,6E)-7-(3,4-dimethoxyphenyl)-3,5-dioxohepta-1,6-dien-1-yl)-2-methoxyphenyl piperidine-1-carboxylate 4-((1E,6E)-7-(3,4-dimethoxyphenyl)-3,5-dioxohepta-1,6-dien-1-yl)-2-methoxyphenyl piperidine-1-carboxylate was prepared as described for 4-((1E,6E)-7-(3,4-dimethoxyphenyl)-3,5-dioxohepta-1,6-dien-1-yl)-2-methoxyphenyl morpholine-4-carboxylate (51 mg, 40%) as an orange solid. LRMS (M+H+) m/z calculated 494.2. found 494.2. ¹H NMR (CDCl₃, 400 MHz) δ 7.57-7.63 (dd, 2H), 7.07-7.15 (m, 5H), 6.87 (d, 1H), 6.48-6.56 (dd, 2H), 5.84 (s, 1H), 3.93 (s, 3H), 3.91 (s, 3H), 3.86 (s, 3H), 3.50-3.62 (m, 4H), 1.59-1.71 (m, 6H).

Example 5: Preparation of 4-((1E,6E)-7-(4-hydroxy-3-methoxyphenyl)-3,5-dioxohepta-1,6-dien-1-yl)-2-methoxyphenyl dimethylcarbamate

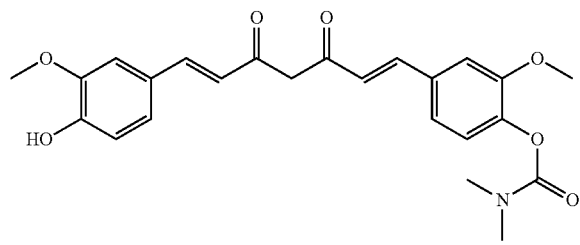 [SMILES: COc1cc(/C=C/C(=O)CC(=O)/C=C/c2ccc(OC(=O)N(C)C)c(OC)c2)ccc1O]

4-((1E,6E)-7-(4-hydroxy-3-methoxyphenyl)-3,5-dioxohepta-1,6-dien-1-yl)-2-methoxyphenyl dimethylcarbamate

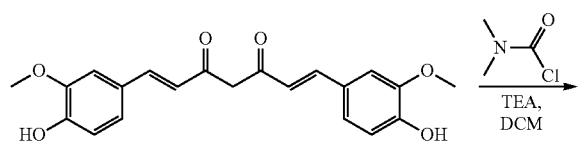

To the solution of (1E,6E)-1,7-bis(4-hydroxy-3-methoxyphenyl)hepta-1,6-diene-3,5-dione (150 mg, 0.4 mmol, 1.0 eq.) in dry DCM (15 mL) were added TEA (81 mg, 0.8 mmol, 2.0 eq.) and dimethylcarbamic chloride (43.8 mg, 0.4 mmol, 1.0 eq.). The reaction mixture was stirred at rt overnight, then washed with water and extracted with CH₂Cl₂ (30 mL×2). The combined organic layers were washed with H₂O, dried over anhydrous Na₂SO₄ and concentrated. The resulting residue was separated by Prep-HPLC to provide 4-((1E,6E)-7-(4-hydroxy-3-methoxyphenyl)-3,5-dioxohepta-1,6-dien-1-yl)-2-methoxyphenyl dimethylcarbamate (50 mg, 28% yield). LRMS (M+H+) m/z calculated 440.2. found 440.2. ¹H NMR (CDCl₃, 400 MHz) δ 7.56 (s, 1H), 7.52 (s, 1H), 6.98-7.07 (m, 6H), 6.87 (d, 1H), 6.40-6.49 (m, 2H), 5.76 (s, 1H), 3.88 (s, 3H), 3.82 (s, 3H), 3.06 (s, 3H), 2.95 (s, 3H).

Example 6: Preparation of 4-((1E,6E)-7-(4-hydroxy-3-methoxyphenyl)-3,5-dioxohepta-1,6-dien-1-yl)-2-methoxyphenyl piperidine-1-carboxylate

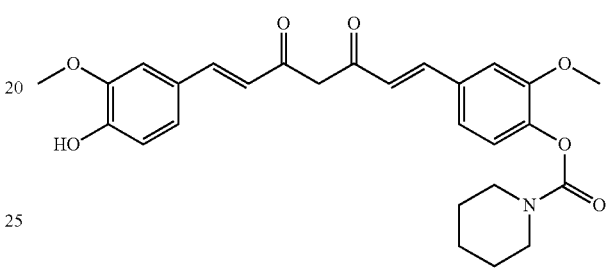

4-((1E,6E)-7-(4-hydroxy-3-methoxyphenyl)-3,5-dioxohepta-1,6-dien-1-yl)-2-methoxyphenyl piperidine-1-carboxylate 4-((1E,6E)-7-(4-hydroxy-3-methoxyphenyl)-3,5-dioxohepta-1,6-dien-1-yl)-2-methoxyphenyl piperidine-1-carboxylate was prepared as described for 4-((1E,6E)-7-(4-hydroxy-3-methoxyphenyl)-3,5-dioxohepta-1,6-dien-1-yl)-2-methoxyphenyl dimethylcarbamate (50 mg, 25% yield). LRMS (M+H+) m/z calculated 480.2. found 480.1. ¹H NMR (CDCl₃, 400 MHz) δ 7.60 (d, 2H), 7.05-7.15 (m, 6H), 6.93 (d, 1H), 6.46-6.56 (m, 2H), 5.82 (s, 1H), 3.95 (s, 3H), 3.88 (s, 3H), 3.51-3.63 (m, 4H), 1.58-1.69 (m, 6H).

Example 7: Preparation of 4-((1E,6E)-7-(4-hydroxy-3-methoxyphenyl)-3,5-dioxohepta-1,6-dien-1-yl)-2-methoxyphenyl morpholine-4-carboxylate

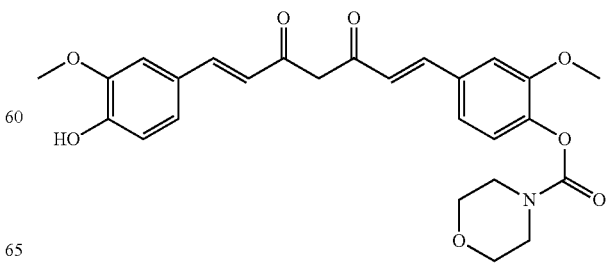

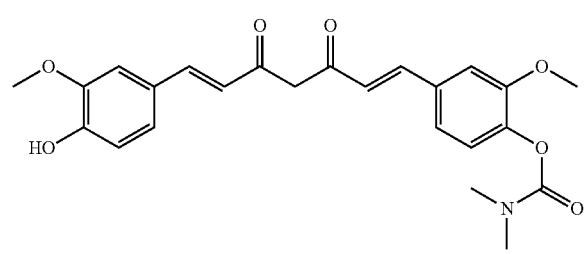

4-((1E,6E)-7-(4-hydroxy-3-methoxyphenyl)-3,5-dioxohepta-1,6-dien-1-yl)-2-methoxyphenyl morpholine-4-carboxylate 4-((1E,6E)-7-(4-hydroxy-3-methoxyphenyl)-3,5-dioxohepta-1,6-dien-1-yl)-2-methoxyphenyl morpholine-4-carboxylate was prepared as described for 4-((1E,6E)-7-(4-hydroxy-3-methoxyphenyl)-3,5-dioxohepta-1,6-dien-1-yl)-2-methoxyphenyl dimethylcarbamate (50 mg, 25% yield). LRMS (M+H$^+$) m/z calculated 482.2. found 482.1. $^1$H NMR (CDCl$_3$, 400 MHz) δ 7.54 (d, 2H), 6.98-7.10 (m, 6H), 6.86 (d, 1H), 6.40-6.50 (m, 2H), 5.76 (s, 1H), 3.88 (s, 3H), 3.84 (s, 3H), 3.51-3.70 (m, 8H).

Example 8: Preparation of 4-((1E,6E)-7-(4-hydroxy-3-methoxyphenyl)-3,5-dioxohepta-1,6-dien-1-yl)-2-methoxyphenyl 4-methylpiperazine-1-carboxylate

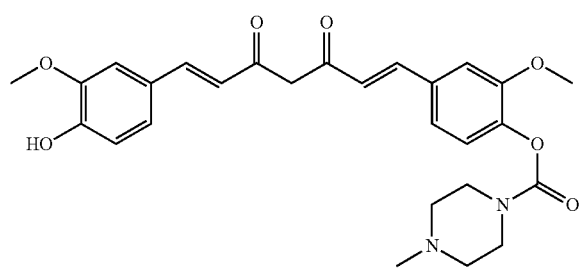 [SMILES: COc1cc(/C=C/C(=O)CC(=O)/C=C/c2ccc(OC(=O)N3CCN(C)CC3)c(OC)c2)ccc1O]

4-((1E,6E)-7-(4-hydroxy-3-methoxyphenyl)-3,5-dioxohepta-1,6-dien-1-yl)-2-methoxyphenyl 4-methylpiperazine-1-carboxylate 4-((1E,6E)-7-(4-hydroxy-3-methoxyphenyl)-3,5-dioxohepta-1,6-dien-1-yl)-2-methoxyphenyl 4-methylpiperazine-1-carboxylate was prepared as described for 4-((1E,6E)-7-(4-hydroxy-3-methoxyphenyl)-3,5-dioxohepta-1,6-dien-1-yl)-2-methoxyphenyl dimethylcarbamate (52 mg, 26% yield). LRMS (M+H+) m/z calculated 495.2. found 495.2. $^1$H NMR (CDCl$_3$, 400 MHz) δ 7.57-7.63 (dd, 2H), 7.05-7.15 (m, 6H), 6.93 (d, 1H), 6.47-6.57 (m, 2H), 5.83 (s, 1H), 4.31-4.53 (m, 2H), 3.95 (s, 3H), 3.88 (s, 3H), 3.51-3.70 (m, 4H), 2.88 (s, 3H), 1.65-1.81 (m, 2H).

Example 9: Preparation of 4-((1E,6E)-7-(4-hydroxy-3-methoxyphenyl)-3,5-dioxohepta-1,6-dien-1-yl)-2-methoxyphenyl piperazine-1-carboxylate

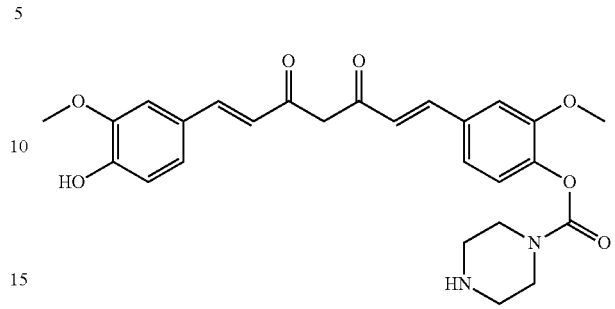

4-((1E,6E)-7-(4-hydroxy-3-methoxyphenyl)-3,5-dioxohepta-1,6-dien-1-yl)-2-methoxyphenyl piperazine-1-carboxylate 4-((1E,6E)-7-(4-hydroxy-3-methoxyphenyl)-3,5-dioxohepta-1,6-dien-1-yl)-2-methoxyphenyl piperazine-1-carboxylate was prepared as described for 4-((1E,6E)-7-(4-hydroxy-3-methoxyphenyl)-3,5-dioxohepta-1,6-dien-1-yl)-2-methoxyphenyl dimethylcarbamate (28 mg, 28.2% yield). LCMS (M+H$^1$) m/z calculated 481.2. found 481.2. $^1$H NMR (CD$_3$OD, 400 MHz) δ 7.51 (d, 2H), 7.25 (s, 1H), 7.13 (d, 2H), 7.01-7.05 (m, 2H), 6.72 (d, 1H), 6.68 (d, 1H), 6.55 (d, 1H), 5.91 (s, 1H), 3.81-3.86 (m, 2H), 3.81 (s, 3H), 3.80 (s, 3H), 3.65-3.73 (m, 2H), 3.20-3.22 (m, 4H).

Example 10: Preparation of 4-((1E,6E)-7-(4-(2-hydroxyethoxy)-3-methoxyphenyl)-3,5-dioxohepta-1,6-dien-1-yl)-2-methoxyphenyl dimethylcarbamate

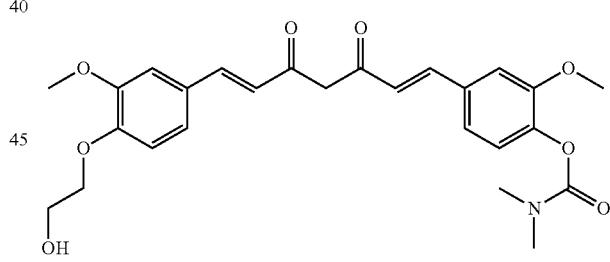

4-((1E,6E)-7-(4-(2-hydroxyethoxy)-3-methoxyphenyl)-3,5-dioxohepta-1,6-dien-1-yl)-2-methoxyphenyl dimethylcarbamate

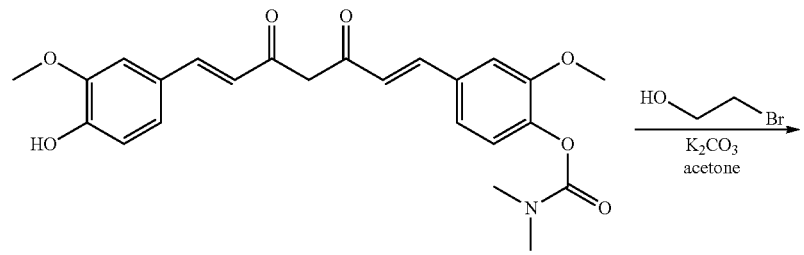

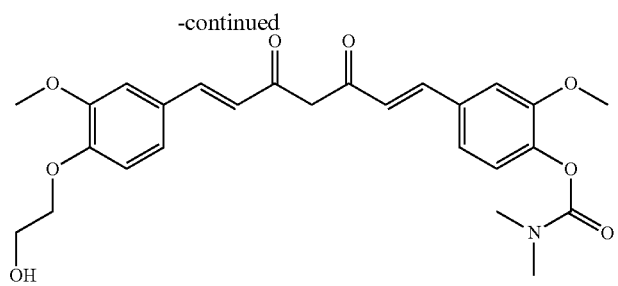

The mixture of 4-((1E,6E)-7-(4-hydroxy-3-methoxyphenyl)-3,5-dioxohepta-1,6-dien-1-yl)-2-methoxyphenyl dimethylcarbamate (88 mg, 0.2 mmol, 1.0 eq), 2-bromoethanol (37.5 mg, 0.3 mmol, 1.5 eq) and $K_2CO_3$ (110 mg, 0.8 mmol, 4.0 eq) in acetone (10 ml) was stirred under reflux for 5 h. Then the mixture was concentrated and The resulting residue was separated by Prep-HPLC to provide 4-((1E,6E)-7-(4-(2-hydroxyethoxy)-3-methoxyphenyl)-3,5-dioxohepta-1,6-dien-1-yl)-2-methoxyphenyl dimethylcarbamate (35 mg, 36.1%). LRMS (M+H$^+$) m/z calculated 484.2. found 484.2. $^1$H NMR (CDCl3, 400 MHz) δ 7.58-7.62 (dd, 2H), 7.07-7.13 (m, 5H), 6.91 (d, 1H), 6.48-6.56 (m, 2H), 5.83 (s, 1H), 4.14-4.17 (t, 2H), 3.96-3.99 (t, 2H), 3.91 (s, 3H), 3.88 (s, 3H), 3.13 (s, 3H), 3.02 (s, 3H).

Example 11: Preparation of 4-((1E,6E)-7-(4-(2-hydroxyethoxy)-3-methoxyphenyl)-3,5-dioxohepta-1,6-dien-1-yl)-2-methoxyphenyl piperidine-1-carboxylate

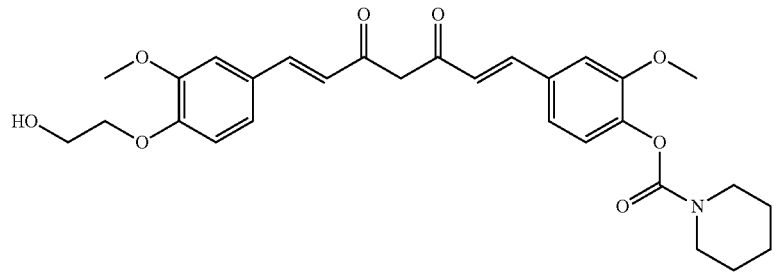 [SMILES: COc1cc(/C=C/C(=O)CC(=O)/C=C/c2ccc(OC(=O)N3CCCCC3)c(OC)c2)ccc1OCCO]

4-((1E,6E)-7-(4-(2-hydroxyethoxy)-3-methoxyphenyl)-3,5-dioxohepta-1,6-dien-1-yl)-2-methoxyphenyl piperidine-1-carboxylate 4-((1E,6E)-7-(4-(2-hydroxyethoxy)-3-methoxyphenyl)-3,5-dioxohepta-1,6-dien-1-yl)-2-methoxyphenyl piperidine-1-carboxylate was prepared as described for 4-((1E,6E)-7-(4-(2-hydroxyethoxy)-3-methoxyphenyl)-3,5-dioxohepta-1,6-dien-1-yl)-2-methoxyphenyl dimethylcarbamate (50 mg, 28%). LRMS (M+H$^1$) m/z calculated 524.2. found 524.2. $^1$H NMR (CDCl$_3$, 400 MHz) δ 7.56-7.61 (dd, 2H), 7.06-7.14 (m, 5H), 6.87 (d, 1H), 6.47-6.53 (dd, 2H), 5.82 (s, 1H), 4.11-4.13 (t, 2H), 3.94-3.97 (t, 3H), 3.89 (s, 3H), 3.87 (s, 3H), 3.49-3.62 (m, 4H), 1.61-1.73 (m, 6H).

Example 12: Equilibrium Solubility

The equilibrium solubility of compounds was measured in aqueous buffer. Excess amount of solid compound was added into buffer solution and the sample was briefly sonicated and then shaken at rt for 24 h. The sample was filtered and the concentration was analyzed by HPLC UV. A standard solution at 0.2 mg/mL was prepared in methanol or acetonitrile for each compound and used as an external standard for quantification. Data for curcumin and illustrative compounds in NaOAc/AcOH buffer (100 mM, pH 5.0) is shown in Table 1.

TABLE 1

| Solubility of Illustrative Compounds | |
|---|---|
| Chemical Name | Solubility (mg/mL) |
| Curcumin | <0.001 |
| 4-((1E,6E)-7-(4-hydroxy-3-methoxyphenyl)-3,5-dioxohepta-1,6-dien-1-yl)-2-methoxyphenyl 4-methylpiperazine-1-carboxylate | 0.018 |
| 4-((1E,6E)-7-(3,4-dimethoxyphenyl)-3,5-dioxohepta-1,6-dien-1-yl)-2-methoxyphenyl 4-methylpiperazine-1-carboxylate | 0.32 |

TABLE 1-continued

| Solubility of Illustrative Compounds | |
|---|---|
| Chemical Name | Solubility (mg/mL) |
| 4-((1E,6E)-7-(4-hydroxy-3-methoxyphenyl)-3,5-dioxohepta-1,6-dien-1-yl)-2-methoxyphenyl piperazine-1-carboxylate | 1.39 |

Example 13: Inhibition of Cell Growth in Tumor Cells

Inhibition of cell growth by compounds was measured using MTT assay (Mosmann, T., Journal of Immunological Methods, 1983, 65, 55-63). Tumor cell lines were purchased from ATCC (American Type Culture Collection, Manassas, Va.). All cell lines were maintained in RPMI 1640 (Hyclone) supplemented with 10% fetal bovine serum (FBS, Hyclone), glutamine (2 mM, Hyclone), and antibiotics (penicillin 100

U/mL and streptomycin 50 g/mL) at 37° C. in a humidified atmosphere of 5% $CO_2$ in air. Taxol (positive control, Sigma) and compounds were dissolved in DMSO (Sigma), and the final concentration of DMSO in the medium was 1%. Tumor cells were plated in 96-well plates at densities from 4000 cells/well of a 96-well plate and allowed to adhere/grow for 24 h. They were then treated with various concentrations of drug for 72 h. 3-(4,5-Dimethylthiazol-2-yl)-2,5-diphenyltetrazolium bromide (MTT, Sigma) was used to determine the number of viable cells at the time of compound addition and the number of cells remaining after 72 h compound exposure. The number of cells remaining after 72 h was compared to the number of viable cells at the time of compound addition by measuring the absorbance at 570 nm, allowing for the calculation of growth inhibition.

All concentrations of compounds were tested in triplicate and controls were averaged over 4 wells. $IC_{50}$ was calculated by plotting the concentration of compound vs the percentage of inhibition in treated wells using GraphPad Prism 5. In some embodiments, the compounds described herein exhibited an $IC_{50}$ for A549 cells of less than 100 uM. In some embodiments, the compounds exhibited an $IC_{50}$ for A549 cells of less than 10 uM. Data for curcumin and illustrative compounds are shown in Table 2.

TABLE 2

Inhibitory Activity of Illustrative Compounds in A549 Cells

| Chemical Name | A549 cell $IC_{50}$ (μM) |
|---|---|
| Curcumin | >30 |
| 4-((1E,6E)-7-(4-hydroxy-3-methoxyphenyl)-3,5-dioxohepta-1,6-dien-1-yl)-2-methoxyphenyl dimethylcarbamate | 2.3 |
| 4-((1E,6E)-7-(4-hydroxy-3-methoxyphenyl)-3,5-dioxohepta-1,6-dien-1-yl)-2-methoxyphenyl piperidine-1-carboxylate | 8.0 |
| 4-((1E,6E)-7-(4-hydroxy-3-methoxyphenyl)-3,5-dioxohepta-1,6-dien-1-yl)-2-methoxyphenyl morpholine-4-carboxylate | 7.2 |
| 4-((1E,6E)-7-(4-hydroxy-3-methoxyphenyl)-3,5-dioxohepta-1,6-dien-1-yl)-2-methoxyphenyl 4-methylpiperazine-1-carboxylate | 3.8 |
| 4-((1E,6E)-7-(3,4-dimethoxyphenyl)-3,5-dioxohepta-1,6-dien-1-yl)-2-methoxyphenyl morpholine-4-carboxylate | 4.6 |
| 4-((1E,6E)-7-(3,4-dimethoxyphenyl)-3,5-dioxohepta-1,6-dien-1-yl)-2-methoxyphenyl 4-methylpiperazine-1-carboxylate | 4.3 |
| 4-((1E,6E)-7-(3,4-dimethoxyphenyl)-3,5-dioxohepta-1,6-dien-1-yl)-2-methoxyphenyl dimethylcarbamate | 10.6 |
| 4-((1E,6E)-7-(4-hydroxy-3-methoxyphenyl)-3,5-dioxohepta-1,6-dien-1-yl)-2-methoxyphenyl piperazine-1-carboxylate | 9.2 |
| 4-((1E,6E)-7-(4-(2-hydroxyethoxy)-3-methoxyphenyl)-3,5-dioxohepta-1,6-dien-1-yl)-2-methoxyphenyl dimethylcarbamate | 9.1 |
| 4-((1E,6E)-7-(4-(2-hydroxyethoxy)-3-methoxyphenyl)-3,5-dioxohepta-1,6-dien-1-yl)-2-methoxyphenyl piperidine-1-carboxylate | 10.9 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A method of inhibiting growth of a cancer cell selected from the group consisting of a colorectal cancer cell, a liver cancer cell, a lung cancer cell, a breast cancer cell and an oral cancer cell, the method comprising administering to the cell a therapeutically effective amount of a compound of Formula I:

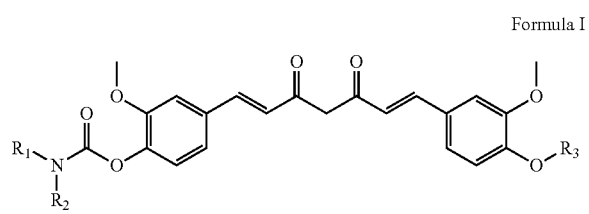

Formula I or a pharmaceutically acceptable salt thereof, wherein:
$R_1$ and $R_2$ are independently chosen from optionally substituted alkyl, optionally substituted cycloalkyl, optionally substituted heterocycloalkyl, optionally substituted aryl, and optionally substituted heteroaryl;
or $R_1$ and $R_2$ may optionally be joined together with any intervening atoms to form an optionally substituted heterocycloalkyl ring; and
$R_3$ is chosen from hydrogen, optionally substituted alkyl, optionally substituted cycloalkyl, optionally substituted heterocycloalkyl, optionally substituted aryl, optionally substituted heteroaryl, optionally substituted acyl, optionally substituted aminocarbonyl, optionally substituted aminosulfonyl, optionally substituted alkoxycarbonyl, and optionally substituted phosphato.

2. The method of claim 1, wherein $R_1$ is chosen from optionally substituted alkyl, optionally substituted cycloalkyl, and optionally substituted heterocycloalkyl.

3. The method of claim 1, wherein $R_2$ is chosen from optionally substituted alkyl, optionally substituted cycloalkyl, and optionally substituted heterocycloalkyl.

4. The method of claim 1, wherein $R_1$ and $R_2$ are independently chosen from optionally substituted alkyl.

5. The method of claim 1, wherein $R_1$ and $R_2$ are joined together to form an optionally substituted 4- to 8-membered heterocycloalkyl ring.

6. The method of claim 5, wherein $R_1$ and $R_2$ are joined together to form an optionally substituted pyrrolidin-1-yl, morpholin-1-yl, piperidin-1-yl, piperazin-1-yl, 1,4-diazepan-1-yl, and 1,4-diazocan-1-yl.

7. The method of claim 1, wherein $R_3$ is chosen from hydrogen, optionally substituted alkyl, optionally substituted cycloalkyl, optionally substituted heterocycloalkyl, optionally substituted aryl, optionally substituted heteroaryl, optionally substituted aminocarbonyl, and optionally substituted phosphato.

8. The method of claim 7, wherein $R_3$ is chosen from hydrogen, optionally substituted lower alkyl, and optionally substituted aminocarbonyl.

9. The method of claim 8, wherein $R_3$ is hydrogen.

10. The method of claim 8, wherein $R_3$ is optionally substituted lower alkyl.

11. The method of claim 10, wherein $R_3$ is lower alkyl substituted with hydroxyl or amino.

12. The method of claim 8, wherein $R_3$ is optionally substituted aminocarbonyl.

13. The method of claim 1, wherein the compound is chosen from:
4-((1E,6E)-7-(4-hydroxy-3-methoxyphenyl)-3,5-dioxohepta-1,6-dien-1-yl)-2-methoxyphenyl dimethylcarbamate, 4-((1E,6E)-7-(4-hydroxy-3-methoxyphenyl)-3,5-dioxohepta-1,6-dien-1-yl)-2-methoxyphenyl piperidine-1-carboxylate,
4-((1E,6E)-7-(4-hydroxy-3-methoxyphenyl)-3,5-dioxohepta-1,6-dien-1-yl)-2-methoxyphenyl 4-hydroxypiperidine-1-carboxylate,
4-((1E,6E)-7-(4-hydroxy-3-methoxyphenyl)-3,5-dioxohepta-1,6-dien-1-yl)-2-methoxyphenyl 4-aminopiperidine-1-carboxylate,
4-((1E,6E)-7-(4-hydroxy-3-methoxyphenyl)-3,5-dioxohepta-1,6-dien-1-yl)-2-methoxyphenyl 3-hydroxypiperidine-1-carboxylate,
4-((1E,6E)-7-(4-hydroxy-3-methoxyphenyl)-3,5-dioxohepta-1,6-dien-1-yl)-2-methoxyphenyl 3-aminopiperidine-1-carboxylate,
4-((1E,6E)-7-(4-hydroxy-3-methoxyphenyl)-3,5-dioxohepta-1,6-dien-1-yl)-2-methoxyphenyl piperazine-1-carboxylate,
4-((1E,6E)-7-(4-hydroxy-3-methoxyphenyl)-3,5-dioxohepta-1,6-dien-1-yl)-2-methoxyphenyl 4-methylpiperazine-1-carboxylate,
4-((1E,6E)-7-(4-hydroxy-3-methoxyphenyl)-3,5-dioxohepta-1,6-dien-1-yl)-2-methoxyphenyl 3-(hydroxymethyl)piperazine-1-carboxylate,
4-((1E,6E)-7-(4-hydroxy-3-methoxyphenyl)-3,5-dioxohepta-1,6-dien-1-yl)-2-methoxyphenyl 3-(hydroxymethyl)-4-methylpiperazine-1-carboxylate,
4-((1E,6E)-7-(4-hydroxy-3-methoxyphenyl)-3,5-dioxohepta-1,6-dien-1-yl)-2-methoxyphenyl morpholine-4-carboxylate,
4-((1E,6E)-7-(4-hydroxy-3-methoxyphenyl)-3,5-dioxohepta-1,6-dien-1-yl)-2-methoxyphenyl 2-(hydroxymethyl)morpholine-4-carboxylate,
4-((1E,6E)-7-(4-hydroxy-3-methoxyphenyl)-3,5-dioxohepta-1,6-dien-1-yl)-2-methoxyphenyl 2-(aminomethyl)morpholine-4-carboxylate,
4-((1E,6E)-7-(4-hydroxy-3-methoxyphenyl)-3,5-dioxohepta-1,6-dien-1-yl)-2-methoxyphenyl pyrrolidine-1-carboxylate,
4-((1E,6E)-7-(4-hydroxy-3-methoxyphenyl)-3,5-dioxohepta-1,6-dien-1-yl)-2-methoxyphenyl 3-hydroxypyrrolidine-1-carboxylate,
4-((1E,6E)-7-(4-hydroxy-3-methoxyphenyl)-3,5-dioxohepta-1,6-dien-1-yl)-2-methoxyphenyl 3-aminopyrrolidine-1-carboxylate,
4-((1E,6E)-7-(4-hydroxy-3-methoxyphenyl)-3,5-dioxohepta-1,6-dien-1-yl)-2-methoxyphenyl 3-(hydroxymethyl)pyrrolidine-1-carboxylate,
4-((1E,6E)-7-(4-hydroxy-3-methoxyphenyl)-3,5-dioxohepta-1,6-dien-1-yl)-2-methoxyphenyl 3-(aminomethyl)pyrrolidine-1-carboxylate,
4-((1E,6E)-7-(4-hydroxy-3-methoxyphenyl)-3,5-dioxohepta-1,6-dien-1-yl)-2-methoxyphenyl 1,4-diazepam-1-carboxylate,
4-((1E,6E)-7-(4-hydroxy-3-methoxyphenyl)-3,5-dioxohepta-1,6-dien-1-yl)-2-methoxyphenyl 4-methyl-1,4-diazepane-1-carboxylate,
4-((1E,6E)-7-(4-hydroxy-3-methoxyphenyl)-3,5-dioxohepta-1,6-dien-1-yl)-2-methoxyphenyl (2-aminoethyl)(methyl)carbamate,
4-((1E,6E)-7-(4-hydroxy-3-methoxyphenyl)-3,5-dioxohepta-1,6-dien-1-yl)-2-methoxyphenyl (2-(dimethylamino)ethyl)(methyl)carbamate,
4-((1E,6E)-7-(4-hydroxy-3-methoxyphenyl)-3,5-dioxohepta-1,6-dien-1-yl)-2-methoxyphenyl dimethylcarbamate,
4-((1E,6E)-7-(3,4-dimethoxyphenyl)-3,5-dioxohepta-1,6-dien-1-yl)-2-methoxyphenyl 3-aminopiperidine-1-carboxylate,
4-((1E,6E)-7-(4-(2-hydroxyethoxy)-3-methoxyphenyl)-3,5-dioxohepta-1,6-dien-1-yl)-2-methoxyphenyl 3-aminopiperidine-1-carboxylate,
4-((1E,6E)-7-(4-(2-hydroxyethoxy)-3-methoxyphenyl)-3,5-dioxohepta-1,6-dien-1-yl)-2-methoxyphenyl 4-aminopiperidine-1-carboxylate,
4-((1E,6E)-7-(3,4-dimethoxyphenyl)-3,5-dioxohepta-1,6-dien-1-yl)-2-methoxyphenyl piperazine-1-carboxylate,
4-((1E,6E)-7-(4-(2-hydroxyethoxy)-3-methoxyphenyl)-3,5-dioxohepta-1,6-dien-1-yl)-2-methoxyphenyl piperazine-1-carboxylate,
4-((1E,6E)-7-(4-((dimethylcarbamoyl)oxy)-3-methoxyphenyl)-3,5-dioxohepta-1,6-dien-1-yl)-2-methoxyphenyl piperazine-1-carboxylate,
((1E,6E)-3,5-dioxohepta-1,6-diene-1,7-diyl)bis(2-methoxy-4, 1-phenylene)bis(piperazine-1-carboxylate),
4-((1E,6E)-7-(3,4-dimethoxyphenyl)-3,5-dioxohepta-1,6-dien-1-yl)-2-methoxyphenyl 4-methylpiperazine-1-carboxylate,
4-((1E,6E)-7-(3,4-dimethoxyphenyl)-3,5-dioxohepta-1,6-dien-1-yl)-2-methoxyphenyl 3-aminopyrrolidine-1-carboxylate,
4-((1E,6E)-7-(4-(2-hydroxyethoxy)-3-methoxyphenyl)-3,5-dioxohepta-1,6-dien-1-yl)-2-methoxyphenyl 3-aminopyrrolidine-1-carboxylate,
4-((1E,6E)-7-(3,4-dimethoxyphenyl)-3,5-dioxohepta-1,6-dien-1-yl)-2-methoxyphenyl 1,4-diazepane-1-carboxylate,
4-((1E,6E)-7-(4-hydroxy-3-methoxyphenyl)-3,5-dioxohepta-1,6-dien-1-yl)-2-methoxyphenyl methyl (2-(pyrrolidin-1-yl)ethyl)carbamate,
4-((1E,6E)-7-(4-hydroxy-3-methoxyphenyl)-3,5-dioxohepta-1,6-dien-1-yl)-2-methoxyphenyl methyl (2-morpholinoethyl)carbamate,
4-((1E,6E)-7-(3,4-dimethoxyphenyl)-3,5-dioxohepta-1,6-dien-1-yl)-2-methoxyphenyl piperidine-1-carboxylate,
4-((1E,6E)-7-(3,4-dimethoxyphenyl)-3,5-dioxohepta-1,6-dien-1-yl)-2-methoxyphenyl morpholine-4-carboxylate,
4-((1E,6E)-7-(4-(2-hydroxyethoxy)-3-methoxyphenyl)-3,5-dioxohepta-1,6-dien-1-yl)-2-methoxyphenyl piperidine-1-carboxylate,
4-((1E,6E)-7-(4-(2-hydroxyethoxy)-3-methoxyphenyl)-3,5-dioxohepta-1,6-dien-1-yl)-2-methoxyphenyl morpholine-4-carboxylate,
4-((1E,6E)-7-(4-(2-hydroxyethoxy)-3-methoxyphenyl)-3,5-dioxohepta-1,6-dien-1-yl)-2-methoxyphenyl dimethylcarbamate,
4-((1E,6E)-7-(4-(2-hydroxyethoxy)-3-methoxyphenyl)-3,5-dioxohepta-1,6-dien-1-yl)-2-methoxyphenyl 4-methylpiperazine-1-carboxylate,
4-((1E,6E)-7-(4-(2-hydroxyethoxy)-3-methoxyphenyl)-3,5-dioxohepta-1,6-dien-1-yl)-2-methoxyphenyl pyrrolidine-1-carboxylate,
4-((1E,6E)-7-(4-(2-hydroxyethoxy)-3-methoxyphenyl)-3,5-dioxohepta-1,6-dien-1-yl)-2-methoxyphenyl (2-aminoethyl)(methyl)carbamate,
4-((1E,6E)-7-(4-(2-hydroxyethoxy)-3-methoxyphenyl)-3,5-dioxohepta-1,6-dien-1-yl)-2-methoxyphenyl (2-(dimethylamino)ethyl)(methyl)carbamate,
4-((1E,6E)-7-(4-(2-hydroxyethoxy)-3-methoxyphenyl)-3,5-dioxohepta-1,6-dien-1-yl)-2-methoxyphenyl methyl (2-(pyrrolidin-1-yl)ethyl)carbamate, 4-((1E,6E)-7-(4-(2-hydroxyethoxy)-3-methoxyphenyl)-3,5-dioxohepta-1,6-dien-1-yl)-2-methoxyphenyl methyl (2-morpholinoethyl)carbamate,
4-((1E,6E)-7-(4-(2-aminoethoxy)-3-methoxyphenyl)-3,5-dioxohepta-1,6-dien-1-yl)-2-methoxyphenyl pyrrolidine-1-carboxylate,
4-((1E,6E)-7-(4-(2-aminoethoxy)-3-methoxyphenyl)-3,5-dioxohepta-1,6-dien-1-yl)-2-methoxyphenyl piperidine-1-carboxylate,
4-((1E,6E)-7-(4-(2-aminoethoxy)-3-methoxyphenyl)-3,5-dioxohepta-1,6-dien-1-yl)-2-methoxyphenyl morpholine-4-carboxylate,
4-((1E,6E)-7-(4-(2-aminoethoxy)-3-methoxyphenyl)-3,5-dioxohepta-1,6-dien-1-yl)-2-methoxyphenyl dimethylcarbamate,
4-((1E,6E)-7-(4-(2-aminoethoxy)-3-methoxyphenyl)-3,5-dioxohepta-1,6-dien-1-yl)-2-methoxyphenyl 4-methylpiperazine-1-carboxylate,
((1E,6E)-3,5-dioxohepta-1,6-diene-1,7-diyl)bis(2-methoxy-4,1-phenylene)bis(4-methylpiperazine-1-carboxylate),
2-methoxy-4-((1E,6E)-7-(3-methoxy-4-((piperidine-1-carbonyl)oxy)phenyl)-3,5-dioxohepta-1,6-dien-1-yl)phenyl piperazine-1-carboxylate,
4-((1E,6E)-7-(4-(((dimethylcarbamoyl)oxy)-3-methoxyphenyl)-3,5-dioxohepta-1,6-dien-1-yl)-2-methoxyphenyl piperazine-1-carboxylate,
2-methoxy-4-((1E,6E)-7-(3-methoxy-4-((piperazine-1-carbonyl)oxy)phenyl)-3,5-dioxohepta-1,6-dien-1-yl)phenyl morpholine-4-carboxylate,
2-methoxy-4-((1E,6E)-7-(3-methoxy-4-((pyrrolidine-1-carbonyl)oxy)phenyl)-3,5-dioxohepta-1,6-dien-1-yl)phenyl piperazine-1-carboxylate, and
2-methoxy-4-((1E,6E)-7-(3-methoxy-4-((4-methylpiperazine-1-carbonyl)oxy)phenyl)-3,5-dioxohepta-1,6-dien-1-yl)phenyl morpholine-4-carboxylate,
and pharmaceutically acceptable salts thereof.

14. The method of claim 1, further comprising administering a second therapeutic agent to the cell.

15. A method of treating a cancer selected from the group consisting of colorectal cancer, liver cancer, lung cancer, a breast cancer and oral cancer in a subject in need thereof, the method comprising administering to the subject a therapeutically effective amount of a compound of Formula I:

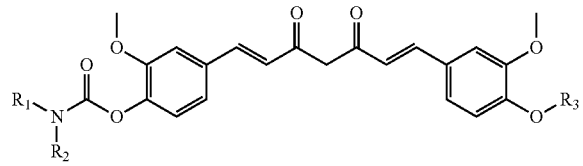

Formula I or a pharmaceutically acceptable salt thereof, wherein:
$R_1$ and $R_2$ are independently chosen from optionally substituted alkyl, optionally substituted cycloalkyl, optionally substituted heterocycloalkyl, optionally substituted aryl, and optionally substituted heteroaryl;
or $R_1$ and $R_2$ may optionally be joined together with any intervening atoms to form an optionally substituted heterocycloalkyl ring; and
$R_3$ is chosen from hydrogen, optionally substituted alkyl, optionally substituted cycloalkyl, optionally substituted heterocycloalkyl, optionally substituted aryl, optionally substituted heteroaryl, optionally substituted acyl, optionally substituted aminocarbonyl, optionally substituted aminosulfonyl, optionally substituted alkoxycarbonyl, and optionally substituted phosphato.

16. The method of claim 15, wherein $R_1$ and $R_2$ are independently chosen from optionally substituted alkyl.

17. The method of claim 15, wherein $R_1$ and $R_2$ are joined together to form an optionally substituted 4- to 8-membered heterocycloalkyl ring.

18. The method of claim 15, wherein $R_3$ is chosen from hydrogen, optionally substituted lower alkyl, and optionally substituted aminocarbonyl.

* * * * *